(12) United States Patent
Moriyama et al.

(10) Patent No.: US 7,016,463 B2
(45) Date of Patent: Mar. 21, 2006

(54) SAMPLE RETAINER FOR X-RAY FLUORESCENCE ANALYSIS, X-RAY FLUORESCENCE ANALYZING METHOD USING THE SAME AND X-RAY FLUORESCENCE SPECTROMETER THEREFOR

(75) Inventors: Takao Moriyama, Takatsuki (JP); Michiko Inoue, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 54 days.

(21) Appl. No.: 10/500,845

(22) PCT Filed: Mar. 31, 2004

(86) PCT No.: PCT/JP2004/004736

§ 371 (c)(1),
(2), (4) Date: Jul. 7, 2004

(87) PCT Pub. No.: WO2005/012889

PCT Pub. Date: Feb. 10, 2005

(65) Prior Publication Data

US 2005/0232393 A1  Oct. 20, 2005

(30) Foreign Application Priority Data

Aug. 1, 2003  (JP) .............................. 2003-285041

(51) Int. Cl.
*G01N 23/223* (2006.01)
(52) U.S. Cl. ............................ 378/47; 378/66; 378/45; 422/58
(58) Field of Classification Search ................. 378/42, 378/44, 45, 47, 66, 79, 208; 422/58, 82.07, 422/82.08; 435/29; 356/246, 244
See application file for complete search history.

(56) References Cited

U.S. PATENT DOCUMENTS

| 4,587,666 | A | * | 5/1986 | Torrisi et al. .................. 378/47 |
| 4,595,561 | A | * | 6/1986 | Thornton et al. ............. 422/58 |
| 5,958,345 | A | * | 9/1999 | Turner et al. ................ 422/104 |
| 2001/0024805 | A1 | * | 9/2001 | Williams et al. .............. 435/29 |

OTHER PUBLICATIONS

Patent Astracts of Japan, Publication No. 2003-090810, Mar. 28, 2003; Nakamura Hideki.

(Continued)

*Primary Examiner*—Edward J. Glick
*Assistant Examiner*—Irakli Kiknadze
(74) *Attorney, Agent, or Firm*—Sughrue Mion, PLLC

(57) ABSTRACT

To provide a sample retainer for X-ray fluorescence analysis, which is used in pretreating a liquid sample and then in X-ray fluorescence analysis of contents of such liquid sample, can sufficiently improve the limit of detection by suppressing the background and, also, allowing the fluorescent X-rays of a high intensity to be emitted uniformly, the sample retainer 5 comprises a ring-shaped pedestal 2; a hydrophobic film 3 of a thickness smaller than 10 μm and having a peripheral portion 3a held by the pedestal and also having a transmitting portion 3b for passage of X-rays therethrough; and a sheet-like liquid absorbent element 4 applied to the transmitting portion 3b of the hydrophobic film 3 and having a thickness within the range of 1 to 100 μm; wherein a liquid sample 1 is adapted to be dispensed dropwise onto and dried on the liquid absorbent element 4b with contents of the liquid sample 1 consequently retained thereon.

5 Claims, 6 Drawing Sheets

OTHER PUBLICATIONS

Patent Abstracts of Japan, Publication No. 2003-090810; Mar. 28, 2003; Shimadzu Corp.

Patent Abstracts of Japan, Publication No. 07-055733; Mar. 3, 1995; Rigaku Ind Co.

"Keiko x-sen ni yoru Suiyoekichu no Biryo Genso no Bunseki", Takao Moriyama, et al., The Society of Chemical Engineers, Japan Dai 69, Mar. 2, 2004; p. 759.

* cited by examiner

SAMPLE RETAINER FOR X-RAY FLUORESCENCE ANALYSIS, X-RAY FLUORESCENCE ANALYZING METHOD USING THE SAME AND X-RAY FLUORESCENCE SPECTROMETER THEREFOR

BACKGROUND OF THE INVENTION

1. Field of the Invention

The present invention relates to a sample retainer for X-ray fluorescence analysis, which is used in pretreating a liquid sample and then in X-ray fluorescence analysis of contents of such liquid sample, an X-ray fluorescence analyzing method of utilizing such sample retainer and an X-ray fluorescence spectrometer therefore.

2. Description of the Prior Art

Hitherto, as a technique to perform X-ray fluorescence analysis for pretreating a liquid sample and analyzing contents contained in such liquid sample, a filter paper drop method (micro-droplet method) is known, in which the liquid sample is dispensed dropwise onto and dried on a filter paper so that the liquid sample can be not only concentrated, but also retained on such filter paper. However, since the filter paper has a thickness of a few hundred micrometer, scattered X-rays of the primary X-rays occurs considerable, resulting in increase of the background. Also, considering the liquid absorption capacity of the filter paper, only 50 to 100 microliter of the liquid sample can be dispensed dropwise at a time and, in the case of a trace quantity of contents, the intensity of fluorescent X-rays which will be emitted from contents concentrated on the filter paper and will subsequently be sensed by a detector may not be insufficient even though dropwise dispense and drying are repeated a number of times before the filter paper is excessively deformed. In other words, the gradient of the calibration curve (a constant associated with the fluorescent X-ray intensity, which is used in the equation of the calibration curve indicative of the concentration of the contents in the liquid sample) does not decrease sufficiently. Accordingly, the limit of detection (LLD) shown in the following equations is, for example, about a few hundred ppb in a region of heavy elements required in environmental analysis and cannot be regarded sufficient.

$$LLD = 3 \times b \times \sigma_{BG} \quad (1)$$

$$\sigma_{BG} = (I_{BG}/(1000 \times t))^{1/2} \quad (2)$$

wherein b represents the gradient of the calibration curve, IBG represents the intensity (kcps) of the background X-rays and t represents the length of measurement time (second).

Accordingly, in order to improve the limit of detection within the bounds of the limited length of measurement time and, also, within the bounds of constant applied voltage and current, there are two ways available, in which the contents of the liquid sample are concentrated so that the sensitivity can increased to thereby improve the gradient of the calibration curve (i.e., to minimize the value of the gradient of the calibration curve. In other words, the contents are concentrated as much as possible so that the fluorescent X-rays emitted therefrom and subsequently sensed by the detector can be increased.) and in which the intensity of the background X-rays is minimized, respectively.

In order to improve the limit of detection based on these, there is a technique in which a polymer film of about 0.5 μm in thickness is formed with a vapor deposited film of, for example, carbon so that a liquid sample can be dispensed dropwise onto and subsequently dried on the area of the polymer film, where the vapor deposited film has been formed, so that contents of the liquid sample can be retained thereon. (See the Japanese Laid-open Patent Publication No. 2003-90810.)

However, since the vapor deposited film is extremely thin and has its diameter limited to about 2 mm in order for the liquid sample to be uniformly concentrated, the amount of the liquid sample that can be dispensed dropwise at a time is equal to or smaller than the amount that can be dispensed dropwise onto the filter paper. Accordingly, although the background can be reduced by the utilization of the polymer film and the vapor deposited film smaller in thickness than the filter paper, the intensity of the fluorescent X-rays that can be obtained does not increase and, therefore, improvement of the limit of detection is not sufficient. Also, with a small surface area of the vapor deposited film, even though dropwise dispensing and drying are repeated to concentrate a large amount of the contents, there are possibilities that the liquid sample cannot be retained stably and that the background will increase as a result of emission of a large amount of scattered X-rays as a result of crystallization of the contents. It is to be noted that if the surface area of the vapor deposited film is increased in order to increase the amount to be dispensed dropwise so that the intensity of the fluorescent X-rays can be increased, concentration will become uneven and emission of the fluorescent X-rays will then become uneven and unstable. (Paragraph 0019 in the previously mentioned publication.)

SUMMARY OF THE INVENTION

The present invention has been devised with the foregoing problems taken into consideration and is intended to provide what, in a sample retainer for X-ray fluorescence analysis, which is used in pretreating a liquid sample and then in X-ray fluorescence analysis of contents of such liquid sample, an X-ray fluorescence analyzing method utilizing such sample retainer and an X-ray fluorescence spectrometer therefore, can sufficiently improve the limit of detection by suppressing the background and, also, allowing the fluorescent X-rays of a high intensity to be emitted uniformly.

In order to accomplish the foregoing object, the sample retainer for X-ray fluorescence analysis according to a first aspect of the present invention is for use in pretreating a liquid sample and then in X-ray fluorescence analysis of contents of such liquid sample, and includes a ring-shaped pedestal, a hydrophobic film of a thickness smaller than 10 μm and having a peripheral portion held by the pedestal and also having a transmitting portion for passage of X-rays therethrough, and a sheet-like liquid absorbent element applied to the transmitting portion of the hydrophobic film and having a thickness within the range of 1 to 100 μm; wherein a liquid sample is adapted to be dispensed dropwise onto and dried on the liquid absorbent element with contents of the liquid sample consequently retained thereon.

According to this first aspect of the present invention, in the first place, since the hydrophobic film and the liquid absorption element, that are irradiated with primary X-rays, have a sufficiently small thickness, it is possible to decrease the scattered X-rays to thereby suppress the background. On the other hand, since with the liquid absorbent element having a proper thickness and applied to the hydrophobic film, a sufficient amount of the liquid sample can be retained and can be uniformly concentrated, it is possible to generate uniformly the fluorescent X-rays of a high intensity. Accordingly, the detection limit can be sufficiently improved.

In this first aspect of the present invention, the use is preferred of polyester (for example, polyethylene terephthalate), polypropylene or polyimide for the hydrophobic film and paper can be used for the liquid absorption element and, in addition, the use is preferred of a paper containing a porous powder, for example, talcum powder (a powder of talc).

The X-ray fluorescence analyzing method according to a second aspect of the present invention makes use of the sample retainer for the X-ray fluorescence analysis according to the first aspect of the present invention and includes causing a liquid sample to be dispensed dropwise onto and dried on the liquid absorption element so that contents of the liquid sample can be retained thereon, irradiating an area of the liquid absorption element with primary X-rays so that generated secondary X-rays can be measured.

The X-ray fluorescence spectrometer according to a third aspect of the present invention makes use of the sample retainer for the X-ray fluorescence analysis according to the first aspect of the present invention and includes a source of X-rays for irradiating an area of the liquid absorption element, where the liquid sample is dispensed dropwise onto and dried on the liquid absorption element with contents of the liquid sample consequently retained thereon, and a detecting device for measuring the intensity of the secondary X-rays emitted from that area of the liquid absorption element.

According to the second and third aspects of the present invention, since the sample retainer for the X-ray fluorescence analysis according to the first aspect of the present invention is utilized, function and effects similar to those in the first aspect of the present invention can be obtained.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
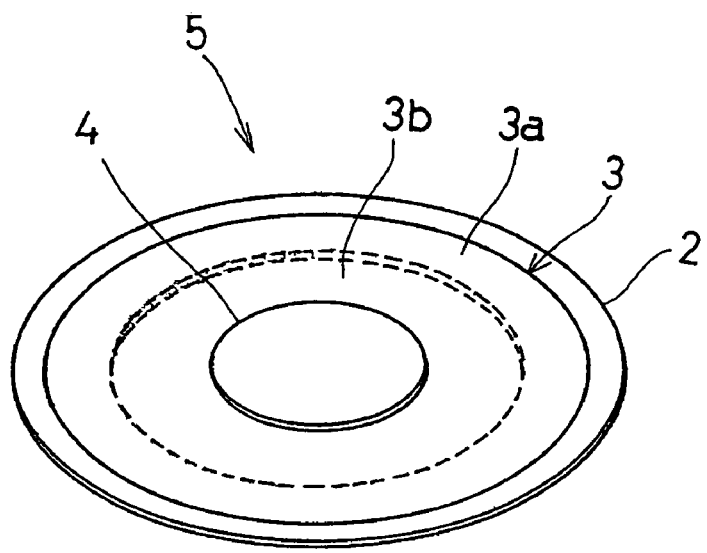
FIG. 1 is a perspective view of a sample retainer for the X-ray fluorescence analysis, which is a first embodiment of the present invention.

In the first place, a sample retainer for the X-ray fluorescence analysis which is a first embodiment of the present invention will be described. This sample retainer is used in pretreating a liquid sample and then in X-ray fluorescence analysis of contents of such liquid sample and includes, as shown in FIG. 1, a ring-shaped pedestal 2 for stably holding a hydrophobic film and made of a resinous material such as, for example, polyethylene or polystyrene, the hydrophobic film 3 of a thickness smaller than 10 $\mu$m and having a peripheral portion 3 held by the pedestal 2 and also having a transmitting portion 3b for passage of X-rays therethrough, and a sheet-like liquid absorbent element 4 applied to the transmitting portion 3b of the hydrophobic film and having a thickness within the range of 1 to 100 $\mu$m, wherein by causing a liquid sample to be dispensed dropwise onto and dried on the liquid absorbent element 4, contents of the liquid sample can be concentrated and retained.

Figure 2:
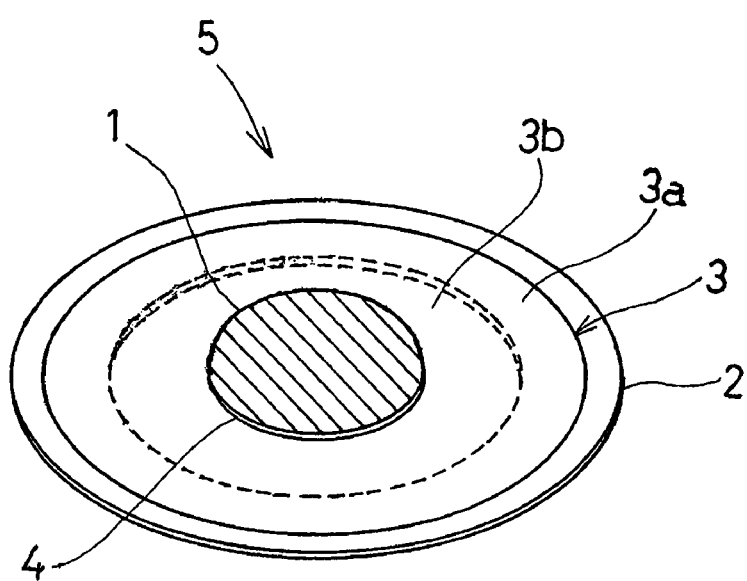
FIG. 2 is a perspective view showing a liquid sample being dispensed dropwise onto the sample retainer.
Figure 3:
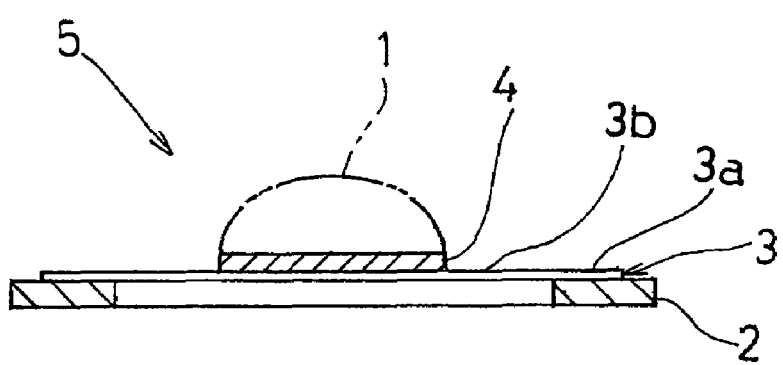
FIG. 3 is a longitudinal sectional view of the sample retainer.

Referring now to FIG. 3 showing a longitudinal sectional view, the hydrophobic film 3 is prepared from polyethylene terephthalate having a thickness of 1.5 $\mu$m and is of a round shape having a diameter substantially equal to the outer diameter of the pedestal 2 (for the purpose of illustration and facilitating a better understanding, shown on a reduced scale), with the peripheral portion 3a retained in tight contact with the pedestal 2. A portion of the hydrophobic film 3 other than the peripheral portion 3a is the transmitting portion 3b for passage of X-rays therethrough. In FIG. 1 and FIG. 2 as will be mentioned later, although an inner perimeter of the pedestal 3 is shown by the broken line as it is hidden beneath the hydrophobic film 3, in reality it is diaphanous and, therefore, viewable. Also, the liquid absorption element 4 is prepared from paper of a few $\mu$m in thickness and containing talcum powder as is the case with, for example, a cosmetic grease-absorbing paper and is of a round shape of 1.8 cm in diameter and pasted to a center portion of the hydrophobic film 3 by means of a spray adhesive (the composition of which contains acrylic rubber (10%), an organic solvent (54%) and an isohexane gas (36%), with dimethyl ether used as a high pressure gas for spraying) sprayed to the backside of the liquid absorption element 4. The bonding agent used for pasting may not be always limited to the spray adhesive, but any bonding agent can be employed, provided that it will not hamper the analysis. It is to be noted that for the purpose of illustration and a better understanding, the thickness of each of parts shown is different from the actual dimension.

In the pretreatment in which the sample retainer 5 is employed, a liquid sample 1 is dispensed dropwise onto the liquid absorption element 4 as shown in FIG. 2. At this time, since the hydrophobic film 3 is present beneath and around the liquid absorption element 4, the liquid sample 1 does not penetrate beneath and around it from the liquid absorption element 4 and can be dispensed dropwise within the range of 200 to 600 $\mu$l by the utilization of a surface tension. By drying the sample retainer 5 onto which the liquid sample 1 has been dispensed dropwise, contents of the liquid sample 1 can be absorbed and retained on the liquid absorption element 4. As a result thereof, the appearance is similar to that shown in FIG. 1 prior to the liquid sample 1 being dispensed dropwise. X-ray fluorescence analysis is carried out by irradiating an area of the liquid absorption element 4 on the sample retainer 5 in this condition with primary X-rays (the placement of the sample retainer 5 on a sample stage of the X-ray fluorescence spectrometer being described later).

Figure 4:
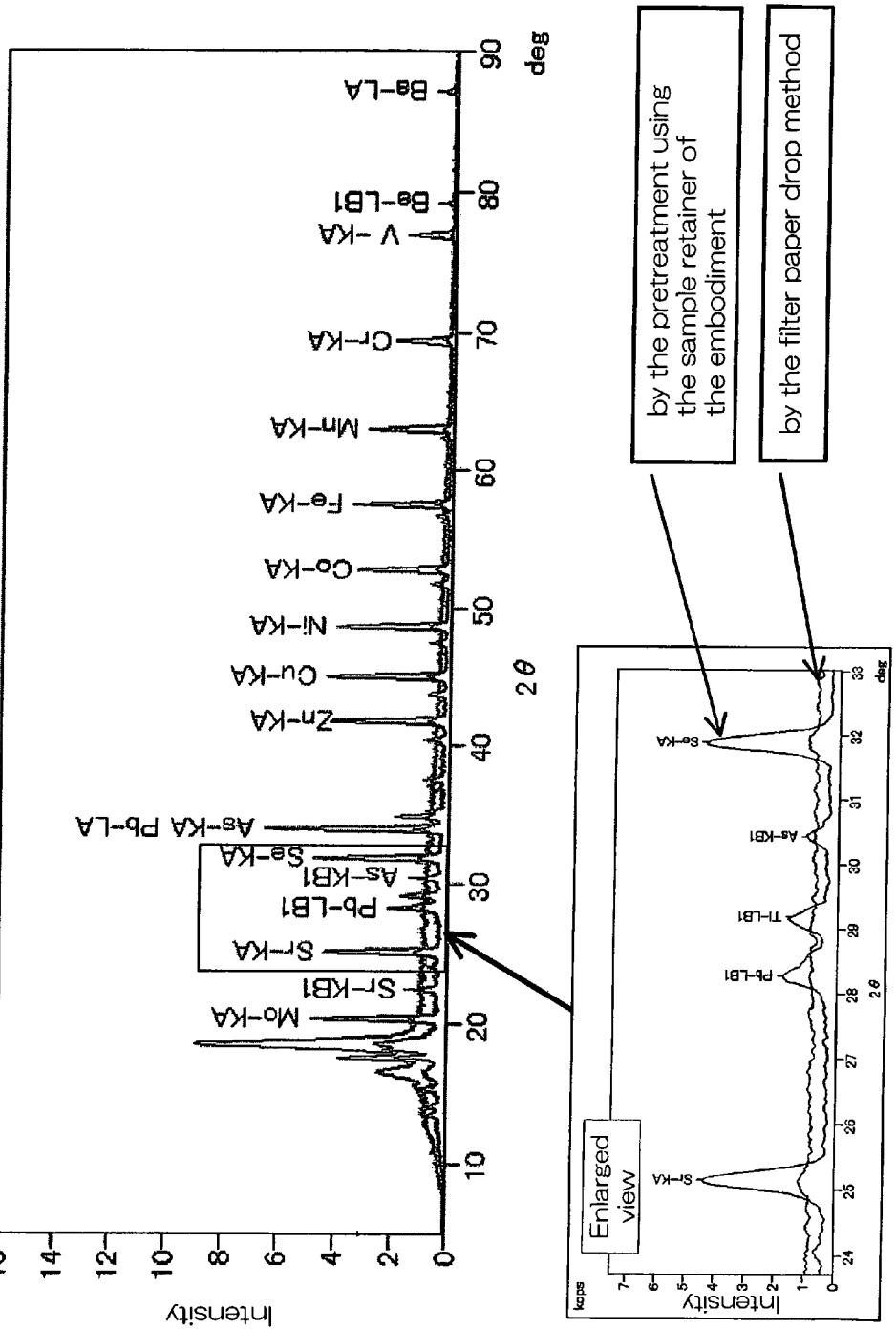
FIG. 4 is a graph showing comparison between a qualitative spectrum resulting from analysis, conducted with the use of the sample retainer, and a qualitative spectrum resulting from analysis conducted with the use of the conventional filter paper.

FIG. 4 illustrates the qualitative spectrum resulting from the analysis when in the conventional filter paper drop method the amount of the liquid sample dispensed dropwise is chosen to be the upper limit of 100 μl, superimposed with the qualitative spectrum resulting from the analysis based on the pretreatment, in which using the sample retainer shown and described in this embodiment the amount of the liquid sample dispensed dropwise is chosen to be 500 μl. According to the graph of FIG. 4, when the sample retainer according to this embodiment is used, it is clear that the background can be reduced down to a value equal to or smaller than half that exhibited when the conventional filter paper is used and, at the same time, a higher intensity of fluorescent X-rays can be obtained.

Also, limits of detection of various elements, when using the sample retainer according to this embodiment the amount of the liquid sample dispensed dropwise is chosen to be 500 μl are tabulated in Table 1 below.

TABLE 1 unit: ppb

| Elements | Detection Limit | Elements | Detection Limit |
|---|---|---|---|
| B  | 30 ppm | Zn | 18  |
| F  | 1 ppm  | As | 16  |
| Na | 76     | Se | 24  |
| P  | 56     | Sr | 25  |
| K  | 12     | Mo | 27  |
| V  | 34     | Ag | 152 |
| Cr | 26     | Cd | 182 |
| Mn | 16     | Sn | 40  |
| Fe | 18     | Sb | 43  |
| Co | 17     | Ba | 105 |
| Ni | 20     | Tl | 81  |
| Cu | 19     | Pb | 76  |

Considering that with the conventional filter peper drop method in which the background is large and the amount of the liquid sample that can be dispensed dropwise is limited to about a value within the range of 50 to 100 μl, the detection limit is limited to a few hundred ppb in the case of a metallic element, a relatively favorable value, it will readily be understood that with the sample retainer according to this embodiment, the detection limit can be improved substantially in the order of a single digit. Also, comparing the values shown in Table 1 with those shown in Table 1 of the previously mentioned Japanese Laid-open Patent Publication No. 2003-90810, although the detection limit is rather low with chromium, the detection limit with the other elements has shown a favorable value.

As discussed above, with the sample retainer for X-ray fluorescence analysis according to this embodiment, in the first place, since the hydrophobic film 3 and the liquid absorption element 4, which are irradiated with the primary X-rays, are sufficiently thin, the background can be suppressed with the scattered X-rays reduced. On the other hand, since with the liquid absorption element 4 of a proper thickness pasted to the hydrophobic film 3, a sufficient amount of the liquid sample 1 can be retained and can be condensed uniformly, it is possible to generate uniformly a high intensity of fluorescent X-rays. Accordingly, the detection limit can be improved satisfactorily.

It is to be noted that the liquid absorption element 4 is held under a predetermined tension at all times when pasted to the hydrophobic film 3 and, therefore, where the amount of the contents is, for example, extremely minute, they can be uniformly and stably retained even though dropwise dispensing and drying are repeated to concentrate the contents in a large quantity. Also, although with the conventional vapor deposited film of a small surface area the contents cannot be easily concentrated sufficiently uniformly because of crystallization, the holder according to this embodiment allows the contents to be sufficiently uniformly concentrated owing to the sheet-like liquid absorption element 4 having a proper thickness and surface area and, therefore, a sufficiently stable quantitative analysis is possible with such light elements as B, F, Na and P.

Figure 5:
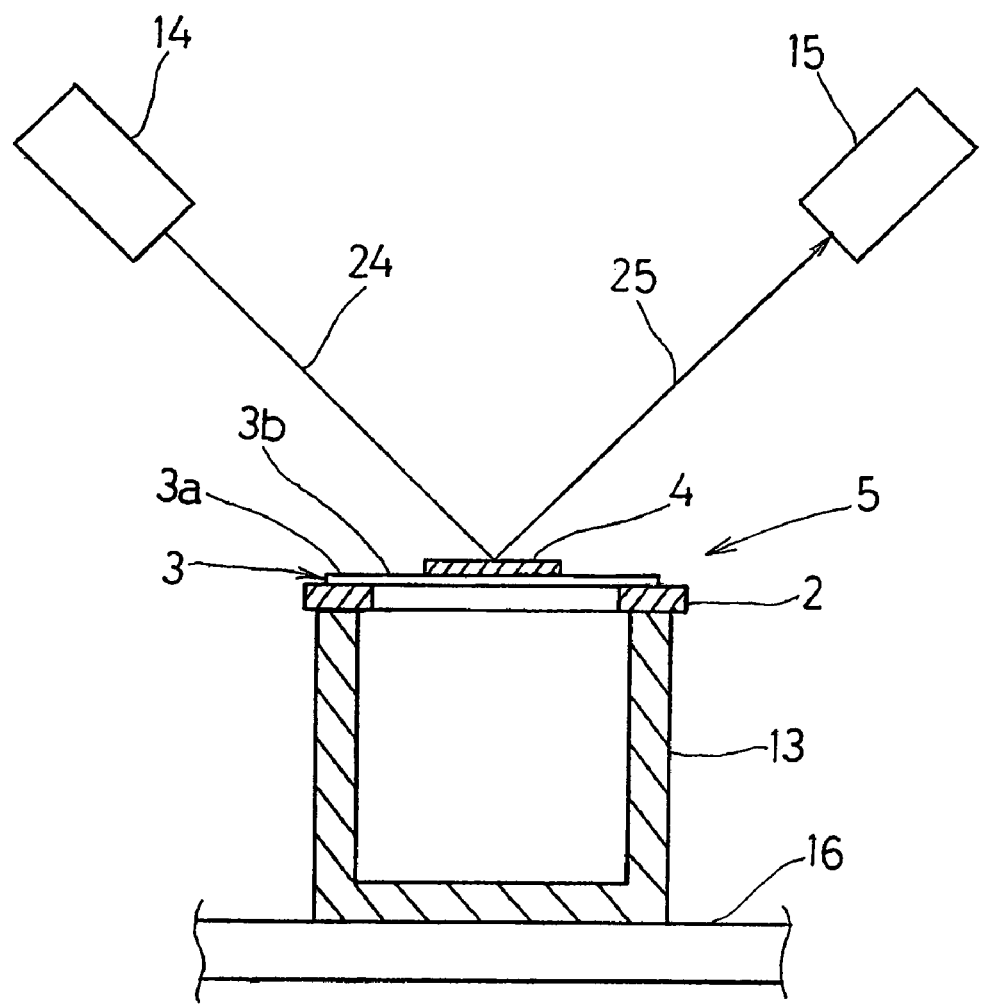
FIG. 5 is a schematic diagram showing an X-ray fluorescence spectrometer according to a third embodiment of the present invention, which is used in the practice of the X-ray fluorescence analyzing method according to a second embodiment of the present invention.

In the next place, the X-ray fluorescence analyzing method according to a second embodiment of the present invention will be described. A X-ray fluorescence spectrometer used in this analyzing method is a third embodiment of the present invention and utilizes, as shown in FIG. 5, the sample retainer 5 for X-ray fluorescence analysis according to the first embodiment and includes a sample stage 16, which is the sample mount on which the sample retainer 5 is placed directly or through a sample holder 13, an X-ray source 14 such as, for example, an X-ray tube for irradiating the area of the liquid absorption element 4, where the contents of the liquid sample 1 (FIG. 3) is retained after the liquid sample 1 (FIG. 3) has been dispensed dropwise and subsequently dried, and a detecting device 15 such as, for example, an X-ray detector for measuring the intensity of secondary X-rays 25 such as, for example, fluorescent X-rays emitted from that area of the liquid absorption element 4.

The X-ray fluorescence analyzing method according to the second embodiment, in which the above described spectrometer is utilized, is a method in which the sample retainer 5 for X-ray fluorescence analysis according to the first embodiment is used and includes, as described previously, retaining the contents of the liquid sample 1 (FIG. 3) by dispensing dropwise onto and then drying the liquid sample 1 (FIG. 3) on the liquid absorption element 4 (FIG. 3), placing the sample retainer 5 in its entirety after this pretreatment on an opening of the cylindrical sample holder (hollow cup) 13 made of Al or Ti and having a bottom closed, and placing the sample holder 13 on the sample stage 16.

The objective of use of such sample holder 13 is to reduce the background by causing anything to be not positioned in the vicinity of the backside of the transmitting portion 3b of the hydrophobic film and, also, to reduce the influence which may be brought about by scattered X-rays of the primary X-rays 24 having penetrated through to the backside of the transmitting portion 3b, at an inner surface of the spectrometer. The sample holder 13 may be merely in the form of an open-ended cylinder.

Figure 6:
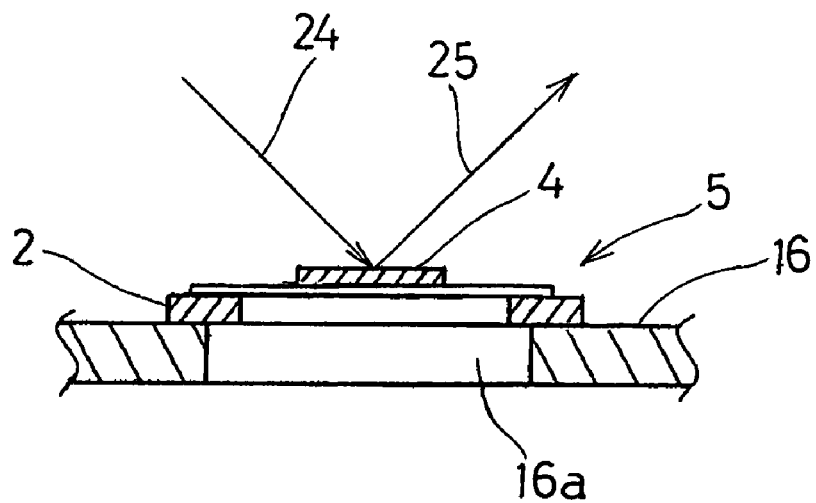
FIG. 6 is a longitudinal sectional view showing a modification of a method of placing the sample retainer on a sample stage.

Also, as shown in FIG. 6, where the sample stage 16 is provided with a through-hole 16a of a size about equal to that of an opening in the pedestal 2, the sample retainer 5 can be placed directly on the sample stage 16 with no sample holder used.

Figure 7:
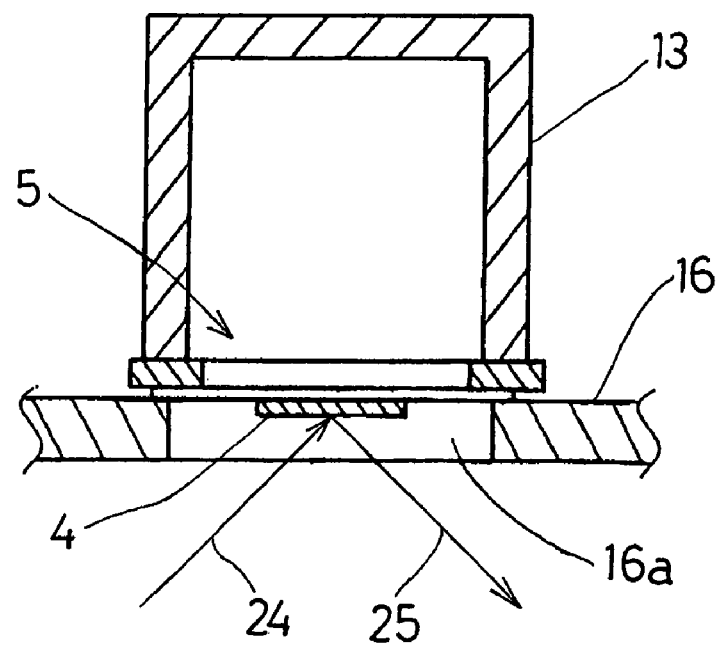
FIG. 7 is a longitudinal sectional view showing a different modification of the method of placing the sample retainer on the sample stage.
Figure 8:
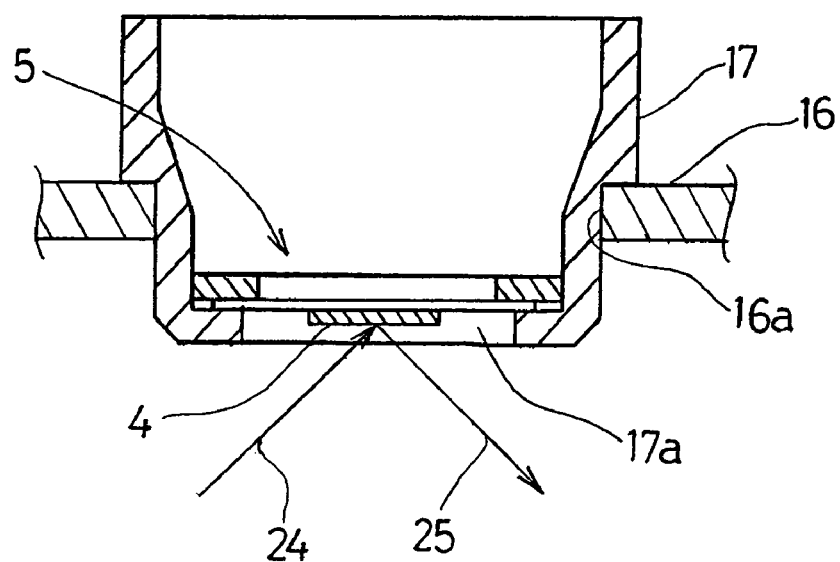
FIG. 8 is a longitudinal sectional view showing a further modification of the method of placing the sample retainer on the sample stage.

While the foregoing applies to so-called downward irradiation in which the primary X-rays irradiate the sample from above, in the case of so-called upward irradiation in which the primary X-rays irradiate the sample from below, as shown in FIG. 7 the sample retainer 5 can be placed on the sample stage 16 while oriented downwardly since the sample stage 16 is provided with the through-hole 16a through which the primary X-rays 24 pass, and the hollow cup 13 can be capped from above so as to orient downwardly in order to reduce the influence brought about by the scattered X-rays. Also, where as the sample mount a sample turret capable of rotating to transport the sample to an analyzing position where the sample is irradiated with the primary X-rays, as shown in FIG. 8, the sample retainer 5 may be inserted into a cylindrical sample holder (support cup) 17, which is closed at one end and has a hole 17a defined at the bottom thereof and also has a lower outer peripheral portion reduced in diameter, with the liquid absorption element 4 oriented downwardly, and the sample holder 17 may then be placed on the sample turret 16 with the reduced diameter portion thereof engaged in the through-hole 16a defined in the sample turret 16 and having a diameter about equal to that of the reduced diameter portion.

As hereinbefore described, by irradiating the area of the liquid absorption element of the sample retainer 5, placed on the sample mount 16, with the primary X-rays, the intensity of the secondary X-rays generated is measured.

With the method and spectrometer according to the second and third embodiments, respectively, since the sample retainer 5 for X-ray fluorescence analysis according to the first embodiment is used, functions and effects similar to those afforded by the first embodiment can be obtained.

What is claimed is:

1. A sample retainer for X-ray fluorescence analysis for use in pretreating a liquid sample and then in X-ray fluorescence analysis of contents of such liquid sample, which retainer comprises
    a ring-shaped pedestal;
    a hydrophobic film of a thickness smaller than 10 $\mu$m and having a peripheral portion held by the pedestal and also having a transmitting portion for passage of X-rays therethrough; and
    a sheet-like liquid absorbent element applied to the transmitting portion of the hydrophobic film and having a thickness within the range of 1 to 100 $\mu$m;
    wherein a liquid sample is adapted to be dispensed dropwise onto and dried on the liquid absorbent element with contents of the liquid sample consequently retained thereon.

2. The sample retainer for X-ray fluorescence analysis as claimed in claim 1;
    wherein the hydrophobic film is made of a material selected from the group consisting of polyester, polypropylene and polyimide; and
    wherein the liquid absorption element is made of paper.

3. The sample retainer for X-ray fluorescence analysis as claimed in claim 2;
    wherein the liquid absorption element is made of paper containing a porous powder.

4. An X-ray fluorescence analyzing method utilizing the sample retainer for X-ray fluorescence analysis as defined in claim 1, which method comprises:
    causing a liquid sample to be dispensed dropwise onto and dried on a liquid absorption element with contents of the liquid sample consequently retained thereon;
    irradiating an area of the liquid absorption element with primary X-rays, to thereby measure an intensity of secondary X-rays generated.

5. An X-ray fluorescence spectrometer utilizing the sample retainer for the X-ray fluorescence analysis as defined in claim 1, which spectrometer comprises:
    a source of X-rays for irradiating an area of a liquid absorption element, where a liquid sample is dispensed dropwise onto and dried on the liquid absorption element with contents of the liquid sample consequently retained thereon; and
    a detecting device for measuring the intensity of the secondary X-rays emitted from that area of the liquid absorption element.

* * * * *